United States Patent [19]

Akagawa et al.

[11] 4,045,659
[45] Aug. 30, 1977

[54] APPARATUS FOR THE EVALUATION OF YARN QUALITIES

[75] Inventors: Masatake Akagawa, Yachiyo; Tsutomu Tamura, Oi, both of Japan

[73] Assignee: Asahi Kasei Kogyo Kabushiki Kaisha, Osaka, Japan

[21] Appl. No.: 674,828

[22] Filed: Apr. 7, 1976

[30] Foreign Application Priority Data

Apr. 7, 1975 Japan .................................. 50-42056

[51] Int. Cl.$^2$ ........................... G06G 7/66; G06G 7/12
[52] U.S. Cl. .................................. 235/151.3; 73/160; 235/151.13; 324/71 R
[58] Field of Search ............... 235/151.3, 193, 92 PD, 235/92 AC, 151.35, 151.13; 73/159, 160; 28/57; 324/77 A, 77 B, 71 R; 356/199, 200

[56] References Cited

U.S. PATENT DOCUMENTS

| 3,594,558 | 7/1971 | Loepfe | 235/151.3 |
|---|---|---|---|
| 3,683,160 | 8/1972 | Windley | 235/151.13 |
| 3,731,069 | 5/1973 | Goto et al. | 235/151.3 |
| 3,763,361 | 10/1973 | Smart | 235/151.13 |
| 3,808,411 | 4/1974 | Hoffmann | 235/193 |
| 3,809,869 | 5/1974 | Gebald | 235/151.3 |
| 3,862,408 | 1/1975 | Bolt | 235/151.13 |
| 3,885,232 | 5/1975 | Goto | 235/151.3 |
| 3,892,951 | 7/1975 | Stutz | 73/160 |

Primary Examiner—Malcolm A. Morrison
Assistant Examiner—Errol A. Krass
Attorney, Agent, or Firm—Armstrong, Nikaido & Marmelstein

[57] ABSTRACT

The invention resides in an improved apparatus for the evaluation of qualities of a running continuous yarn. The apparatus is provided with a capacitive sensor through which the yarn is passed continuously. The apparatus is also provided with a device for extracting from the sensor an output signal with amplitude or frequency components frequency distribution. It is further provided with an electronic calculating device which determines the mean and standard deviation from the foregoing distributory information.

4 Claims, 51 Drawing Figures

FIG.1A
0.1V
FIG.1B
FIG.1C
FIG.1D
FIG.1E
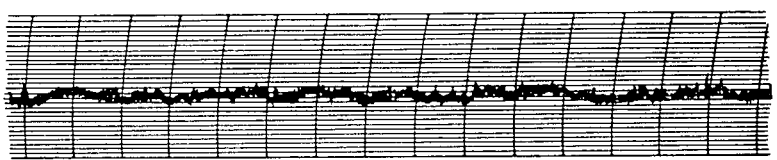
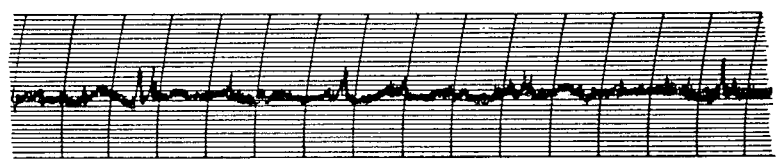
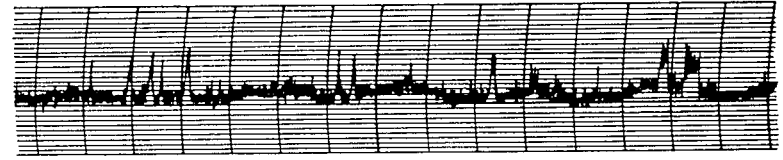
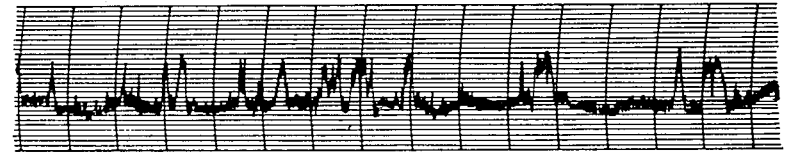
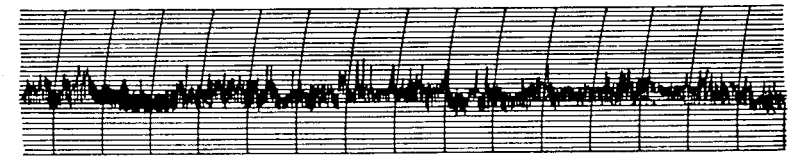

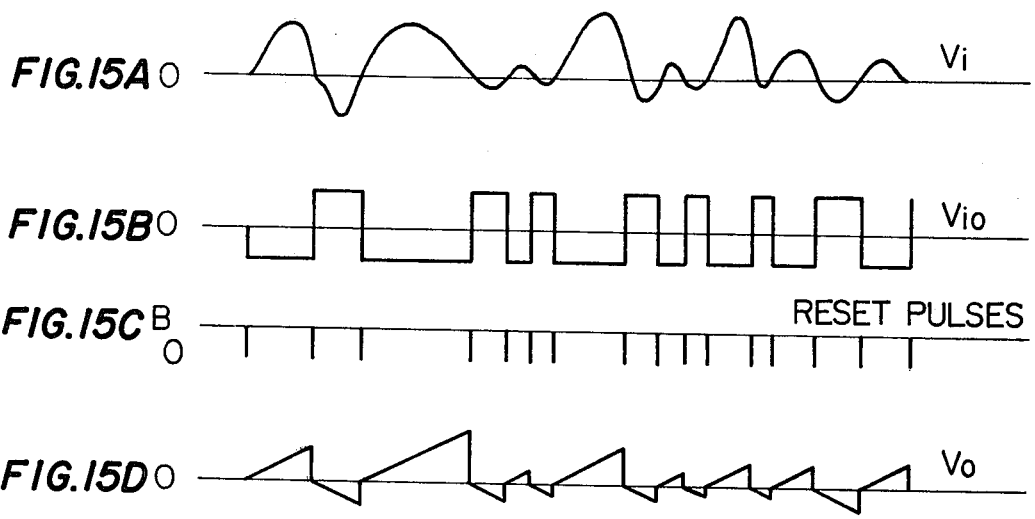
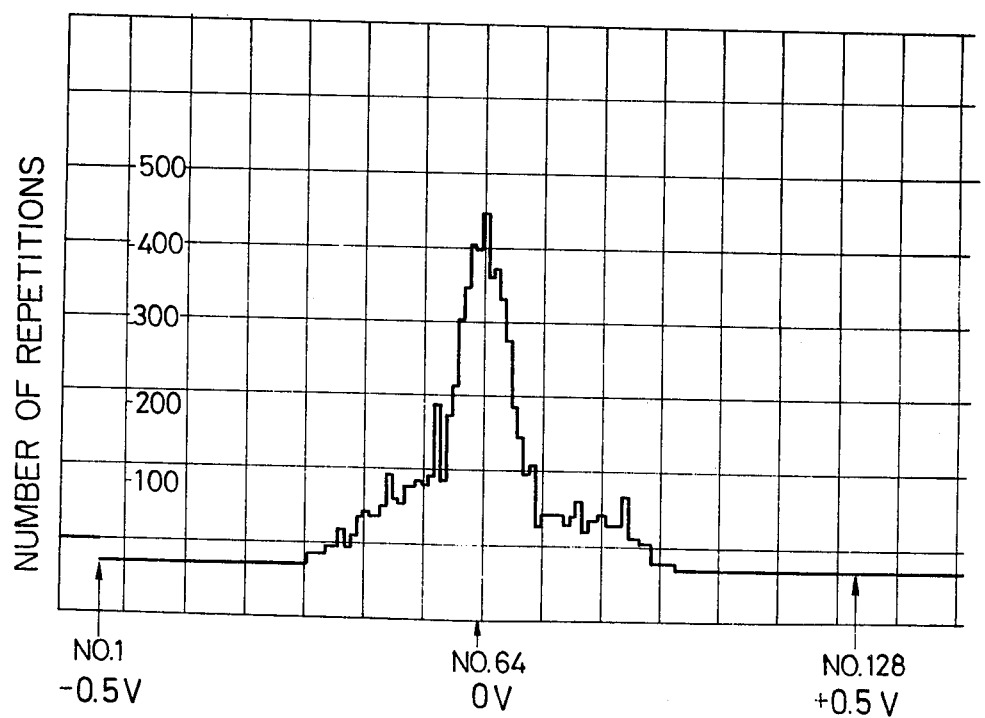

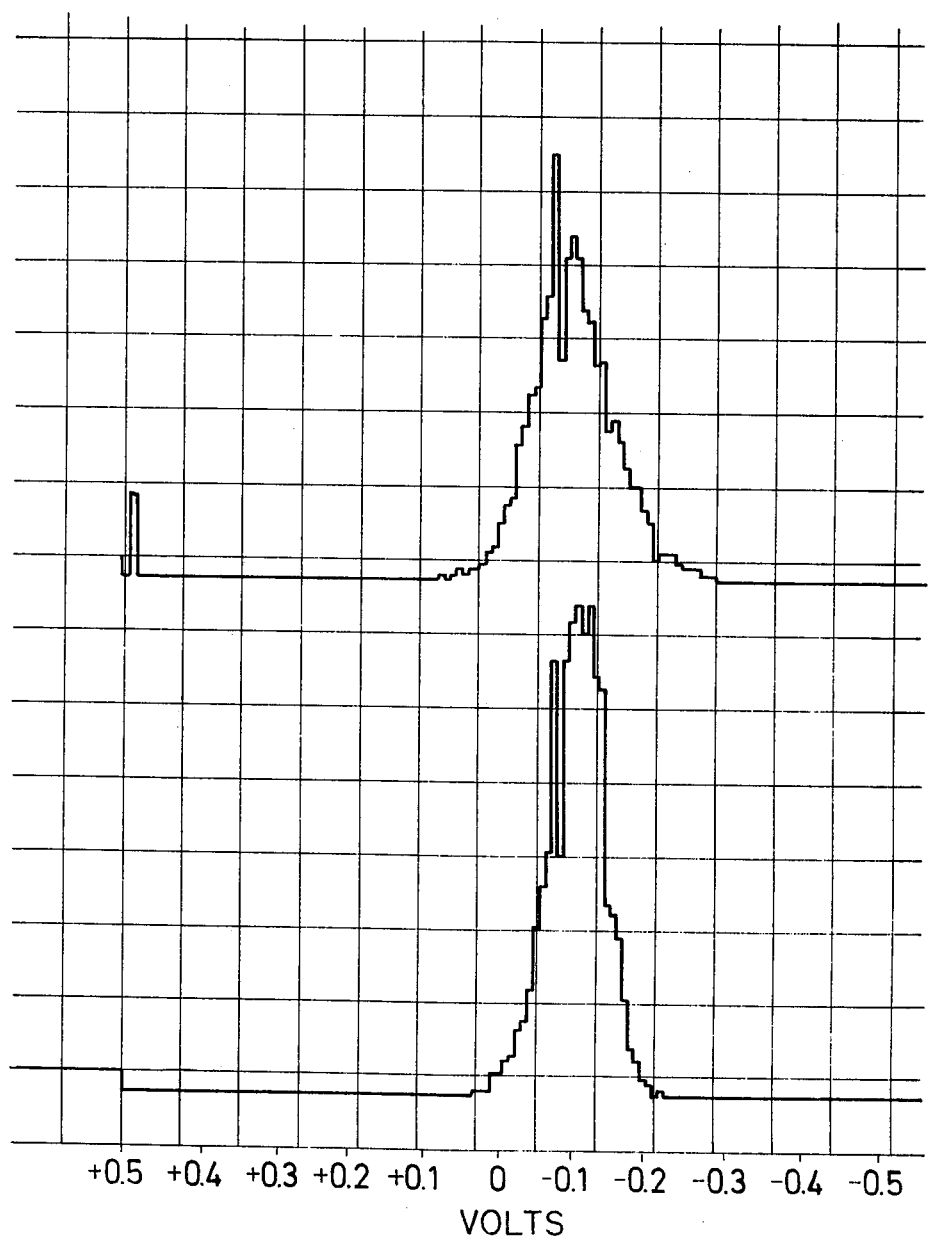

APPARATUS FOR THE EVALUATION OF YARN QUALITIES

BACKGROUND OF THE INVENTION

This invention relates to imrovements in and relating to an apparatus for the evaluation of yarn qualities.

As commonly known among those skilled in the art, yarn qualities comprise mainly physical properties such as strength and elongation values, chemical properties such as dyeing characteristics and morphologic tendency such as slub-formation, regardless of the kind and nature of the yarn, as of natural, synthetic or regenerated fibers.

In present advanced manufacturing process or finishing modes of these fibers, and in each of various and numerous processing steps, such as those of spinning, stretching, false-twisting, threading and sizing, it is possible to manage and control these values roughly within respective specified ranges, while it may be unavoidable that these practical values are subjected to appreciable fluctuation caused by a certain or other reason. It is, therefore, just an ideal to make the yarn quality evaluation, depending upon the degree of fluctuation of these characteristic values.

According to the conventional technique, it has been impossible to make a yarn quality evaluation on line in the yarn manufacturing or processing stage, such as its spinning, stretching, false-twisting, threading, sizing or the like step and concurrently in a combined manner of several yarn qualities, thus the realization of a multi-functional evaluation mode as above, has been a dream of the person skilled in the art.

As is commonly known, the micro-structure of the fiber may be explained briefly as follows:

The man-made fiber comprises a chain of high molecules which are arranged in a highly complicated manner within the fiber which can be said after all as representing a mixture of crystalline regions with amorphous regions.

The mechanical characteristic of the fiber can be expressed by its strength and the degree of elongation, as a representative example and for a practical purpose. Thus, the crystalline region reflects the strength of the yarn, while the amorphous region reflects the degree of elongation thereof. Therefore, yarn strength and its degree of elongation, in combination, can be deemed as the overall characteristics both kinds regions.

When the yarn is subjected to a forced vibration, the amorphous region represents the viscous nature of the yarn, while the crystalline region represents the elastic behavior thereof, thereby the visco-elastic nature of the yarn is the combination of both kinds behaviors.

On the other hand, when the fiber is dyed with a dyestuff, the amorphous region will play an important role. At the amorphous region, the dyestuff is easily diffused therein, regardless of the characteristic of the dyestuff which may have its dyeing performance based substantially upon its chemical or physical behavior. Therefore, the probability of existence of the dyestuff in the amorphous region is substantially higher than in the crystalline region, thus the former region is substantially easier to dye than the latter region.

On the other hand, the crystalline region presents a considerable difficulty in the diffusional affinity to such dyestuff as predominating its physically acting dyeing performance, and thus, this region can be dyed only with difficulty due to the lower prevailing percentage of the above kind of dyestuff. However, such dyestuff as predominating its chemically acting dyeing performance has a high chemical affinity to the crystalline region and is likely to occupy the dyeing seats prevailing in the material crystalline region of the yarn. Thus, this region is more likely to be dyed on account of higher rate of existence of the dye particles.

In the case of dyeing a yarn which is believed to have these crystalline and amorphous regions arranged substantially in a cyclic order when considered theoretically and in an idealized model, by means of a predominantly acting in physical or chemical behavior, the former regions will show a rather apparent difference in the dyed color tone, while the latter regions may show a rather minor difference in the dyed effect and demonstrate no appreciable difference in the color tone.

It has been known for several decades to lead a yarn continuously through a sensing gap formed between and defined by a pair of capacitive electrodes of a sensor unit, to scrutinize yarn mass or denier variation or fluctuation in a precise and continuous way. Those skilled in the art have believed that the electrical outputs from such sensor unit correspond exclusively to the yarn mass or denier variation or fluctuation. However, according to our profound experimentation, it is now found that the electrical output information of the capacitive sensor represents not only the mass or denier variation, but there is also additional and overlapped information which has an intimate corelationship with the visco-elastic characteristic distribution of the yarn under test. The latter characteristics are substantially influenced by the microstructure of the fibers, or more specifically, the corelationship between crystalline and amorphous structures of the yarn molecules. These micro-structural characteristics will have a substantial effect upon the macro-structural behavior of the yarn.

As for the sensor unit commonly used for the above purpose, it has generally the following order of outline dimensions, 8 mm in its length and 5 mm in its height or width. The thickness of a condenser electrode plate is generally about 0.5 mm, while the condenser gap is approximately 0.8 mm. There is provided a stationary yarn guide in close proximity to each end of the gap.

The yarn is guided through the yarn guides and led to travel through the condenser gap at a speed of 100–4,000 meters per minute.

It is observed that the yarn vibrates between the yarn guides, the vibration depending substantially upon the visco-elastic characteristics of the running yarn. With higher visco-elasticity thereof, the vibration amplitude will become larger. According to our finding, the degree of amplitude and frequency components during the yarn vibration plays a significant role in the determination of the yarn characteristic or quality.

In the case of the synthetic fiber yarn, the visco-elasticity will become larger when the yarn largely comprises amorphous regions.

In the dyeing step of the yarn, as was referred to hereinbefore, the dyestuff will be more easily diffused in and among amorphous regions or components of the yarn which characterize the viscous property of the yarn.

On the contrary, the diffusion of dyestuff in and among crystalline regions or components which characterize the elasticity of the yarn, will be rather difficult.

As the physically predominantly acting dyestuffs which are liably dispersed and adsorbed in and by the yarn material, may be raised, among others, direct dyes, disperse dyes and non-ionic dyes as representatives. On the other hand, as the chemically predominantly acting dyestuffs, may be raised among others, cationic dyes, anionic dyes and reactive dyes as representatives.

It has thus been highly difficult to anticipatingly determine the dyeing characteristics of the yarn, especially in advance of the dyeing process and even in the manufacturing step of the yarn and in the manner of the on-line mode.

SUMMARY OF THE INVENTION

The main object of the present invention is to provide an apparatus for the advance and continuous detection of an on-line condition of a yarn, such as mechanical, dyeing and other characteristic distributions, so as to enable an overall and classified evaluation of these characteristics even during the manufacturing stage of the yarn.

According to the presently proposed technique, the output electrical signal from a capacitive sensor is processed in a specific manner. The thus treated electrical signal includes such information as representing the vibration mode of the yarn which appears during the visco-elastic vibration thereof during passage through the sensing condenser gap.

The information includes naturally those of yarn mass variation and its shape-variation.

According to the invention, therefore, the information of yarn vibration is derived and evaluated. In this way, therefore, the yarn characteristic to the chemically predominantly acting dye can be determined in advance of its appearance otherwise upon practical dyeing. Fine and specific coloring characteristics of the yarn, fluctuation of degree of elongation, yarn bulkiness and the like vital and various yarn characteristics can be estimated even in advance of their practical appearance.

These and further objects, features and advantages of the present invention will become more apparent from the following detailed description of the invention to be set forth with reference to the accompanying drawings.

BRIEF DESCRIPTION OF THE DRAWINGS

In the drawings:

FIG. 1 at A, B, C and D are four yarn denier variation curves shown in the form of electrical output signals delivered from a capacitive sensor after passage of respective continuous man-made yarns.

FIG. 15 shows several signal forms appearing at several points of the electronic circuit adopted.

FIGS. 20 - 22 are illustrative of several charts as before.

DETAILED DESCRIPTION OF THE INVENTION

In the following, several data and embodiments of the invention will be described in detail with reference to the accompanying drawings.

In FIG. 1, at A, B, C, D and E, five series of yarn denier signals are representatively shown, as obtained each by passing a continuous yarn through a capacitive sensor which will be shown and described hereinafter.

The yarn was that of a multifilament, 150d/32f, of polyacrylonitrile, manufactured and sold by Asahi Kasei Kogyo Kabushiki Kaisha (Asahi Chemical Industry Co., Ltd.), Osaka, under the trade name of "Pewlon".

The source voltage applied to the sensor unit was so adjusted that the output from the latter will amount to 4 volts when a yarn of 150 deniers is passed through the sensor.

In these graphs, A-E, one vertical gradation was set to 0.1 volt, while one horizontal gradation or scale was selected to correspond to a yarn length of 3.3 meters. Amplifier gain was 400.

In FIG. 2, graphs A-E were taken in an enlarged mode from the foregoing one shown in FIG. 1. These yarn denier signals, A-E in FIG. 2, were treated by the device according to the invention, so as to represent respective yarn denier deviation frequency distribution curves or-charts A'-E', which may be called mathematically as "elementary probability charts". Corresponding standard deviations calculated from these charts, as well as the corresponding coloring performance classification adopted by the Asahi Chemical, are given in the following Table 1.

Table 1

| Group | Yarn Sample | Standard Deviations | Classes of Coloring Performance |
|---|---|---|---|
| I | A | 0.18 | Class 1 to show no uneven coloring |
| | B | 0.26 | Class 2 to show least amount of uneven coloring |
| | C | 0.30 | Class 3 to show slight amount of uneven coloring |
| II | D | 0.42 | Class 5 to show thick color stripes |
| | E | 0.33 | Class 4 to show fine color stripes |

According to the conventional technique, the patterns A, B and C belonging to Group I could not be identified from each other, resulting in similar or one category of output signals.

Further, according to the prior technique, the patterns D and E belonging to Group II could not be specifically identified from each other. It was only possible conventionally to identify the Groups I and II from each other.

It has been demonstrated that according to our comparative experiments, the above yarn quality classification are substantially in coincidence with practical values.

Figure 2A:
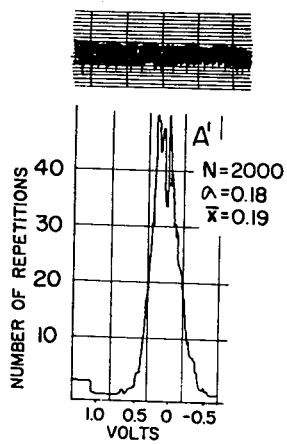
FIG. 2 at A, B, C, D and E shows similar yarn denier variation curves in somewhat enlarged manner when compared with those shown in FIG. 1 and the correspondng amplitude frequency distribution charts at A', B', C', D' and E' obtained upon processing of said denier variation curves according to the present invention.
Figure 2B:
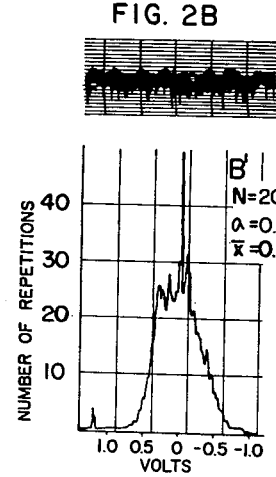
Figure 2C:
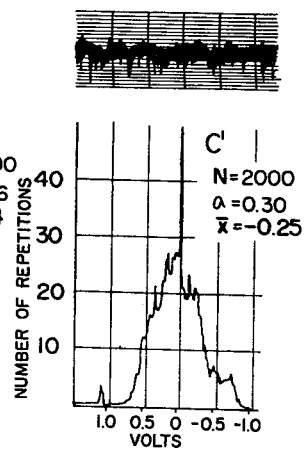
Figure 2D:
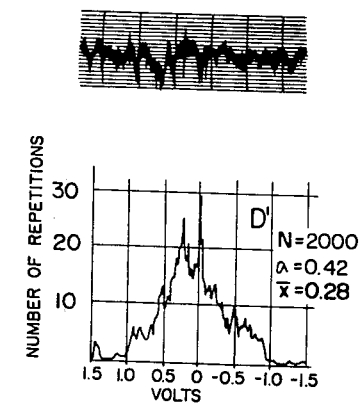
Figure 2E:
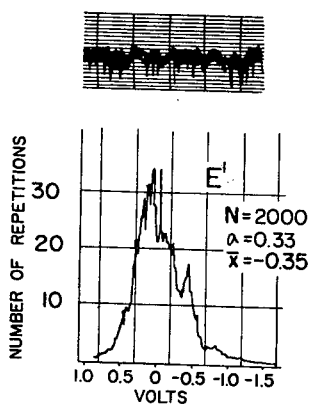
Figure 3:
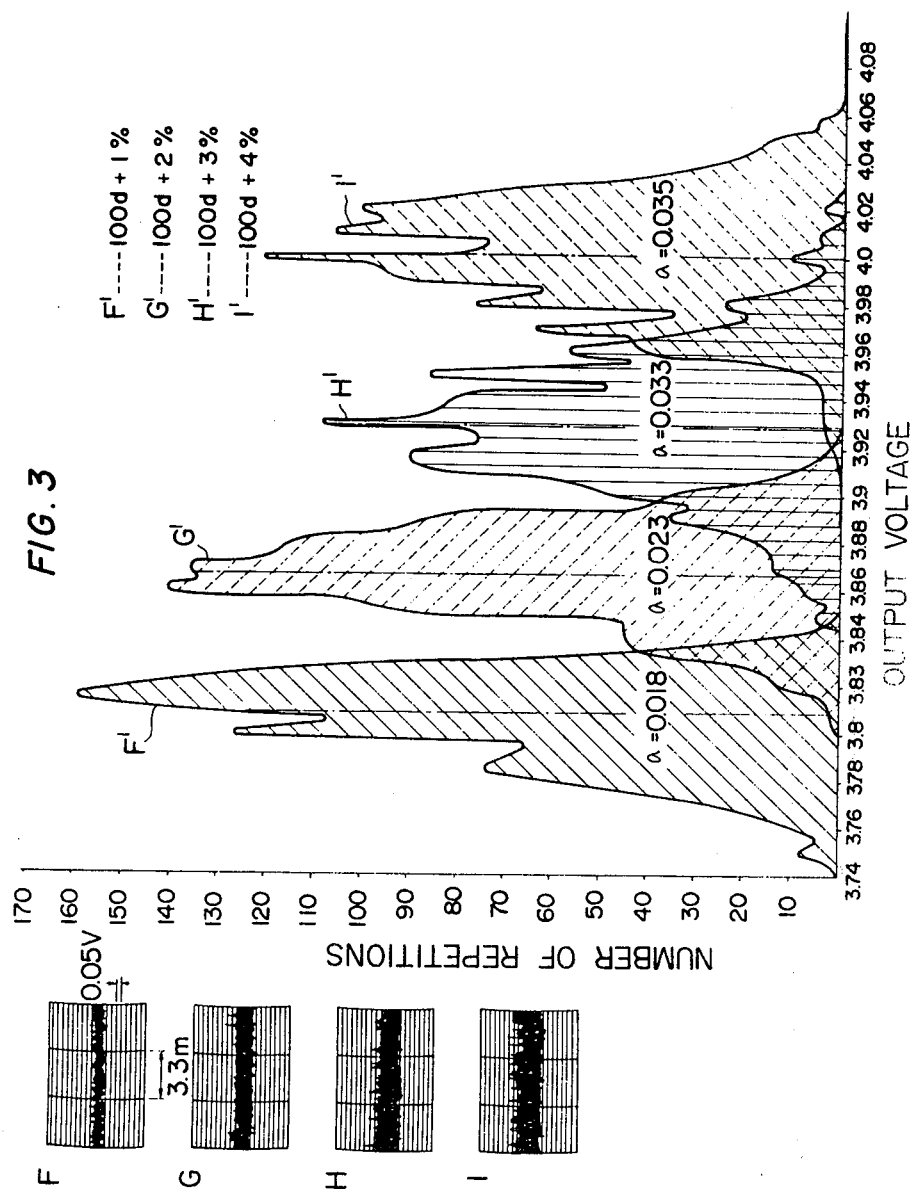
FIG. 3 at F, G, H and I shows four yarn denier variation curves and the respective amplitude frequency distribution charts F', G', H' and I' obtained by the processing of the foregoing.

In a further embodiment, we have treated polyester yarns of 100d/24f which were spun and stretched in similar spinning conditions as before. The experimental results are shown in FIG. 3. In this Figure, F, G, H and I show four series of denier variation values obtained as the respective signal outputs from the same sensor unit. In the case of F, the mean yarn denier showed a 1% increase relative to the standard yarn denier of 100d. In the cases of G, H and I, the yarn samples showed a 2, 3 and 4% increase in the mean over the standard denier value of 100 d, respectively.

In each of these tests, the measured length of the yarn amounted to 2 meters, and the number of samplings amounted to 2,000. Therefore, a sampling yarn length was 1.0 mm.

FIG. 3, at F', G', H' and I' show the respective yarn denier or amplitude-frequency deviation charts as obtained by the treatment of the respective signals F - I according to this invention. In the charts F' - I', several mean values were calculated from these charts. As seen from charts, when the fluctuation is large, the denier increase will be substantially correspondingly large, and vice versa.

In these experiments, each measured yarn length amounted to 1,800 meters. The number of samplings were 12,000. Thus, each sampling length amounted to 0.15 meter.

Figure 4:
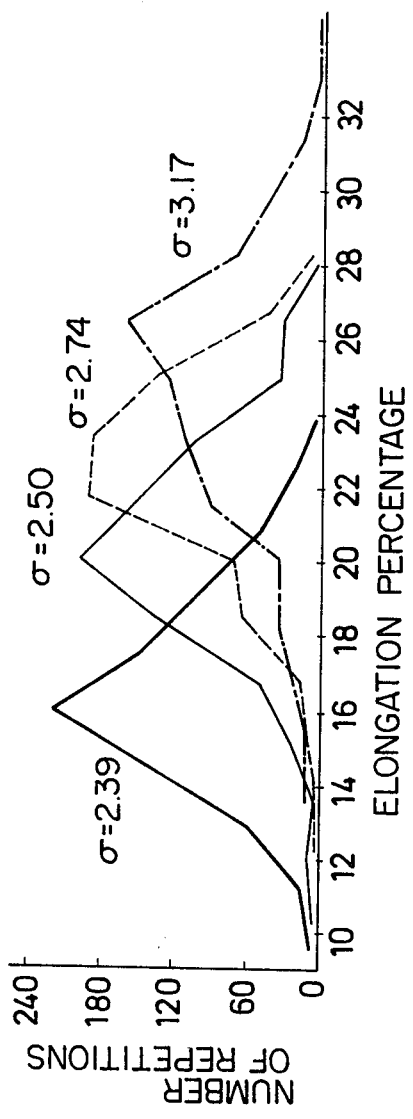
FIG. 4 is a chart showing four different strength-elongation curves.

In FIG. 4, polyester yarn samples corresponding to F - I were measured on a load- or strength-elongation tester and treated according to the invention to obtain the corresponding frequency distribution charts of the load-elongation of the yarn, when seen in FIG. 4 in succession from left to right. The corresponding standard deviations were found as 2.39; 2.50; 2.74 and 3.17, as shown.

On the other hand, the corresponding standard deviations which were calculated from the charts F' - I' were 1.9; 2.2; 3.2 and 3.5, respectively.

Figure 5:
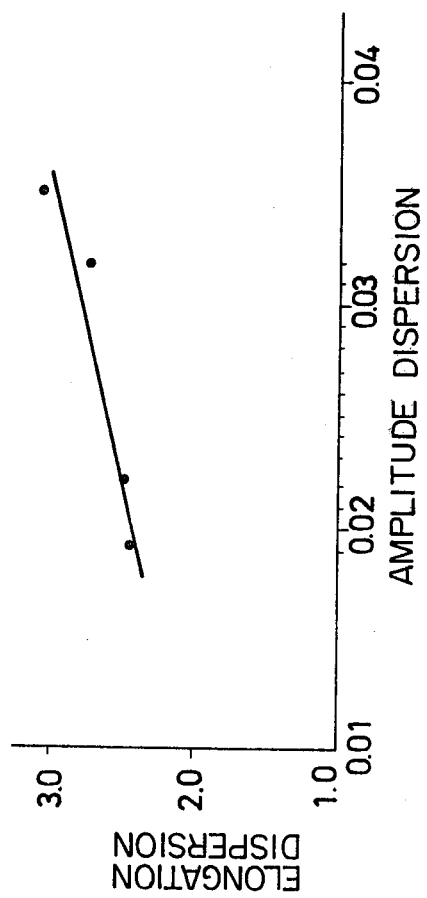
FIG. 5 is a chart of yarn elongation dispersion plotted against amplitude dispersion and based upon the results shown in FIG. 4, as an example.
Figure 6A:
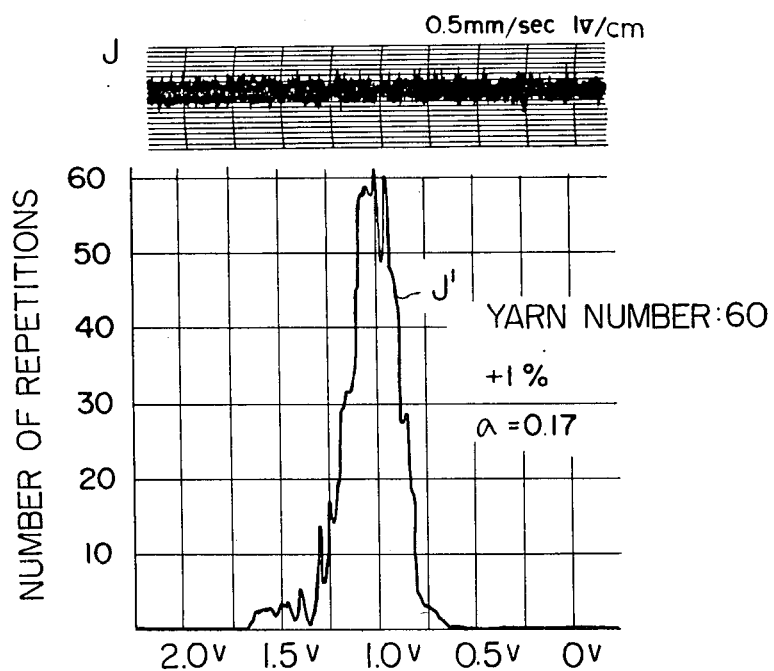
FIG. 6 at J, K, L and M shows several yarn denier variation curves, and the corresponding amplitude frequency distribution charts obtained by the processing thereof, adapted for the determination of the corresponding yarn bulkinesses.
Figure 6B:
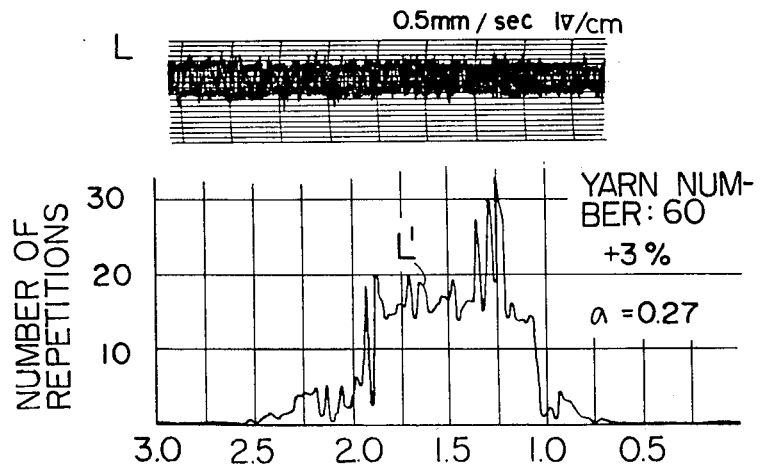
Figure 6C:
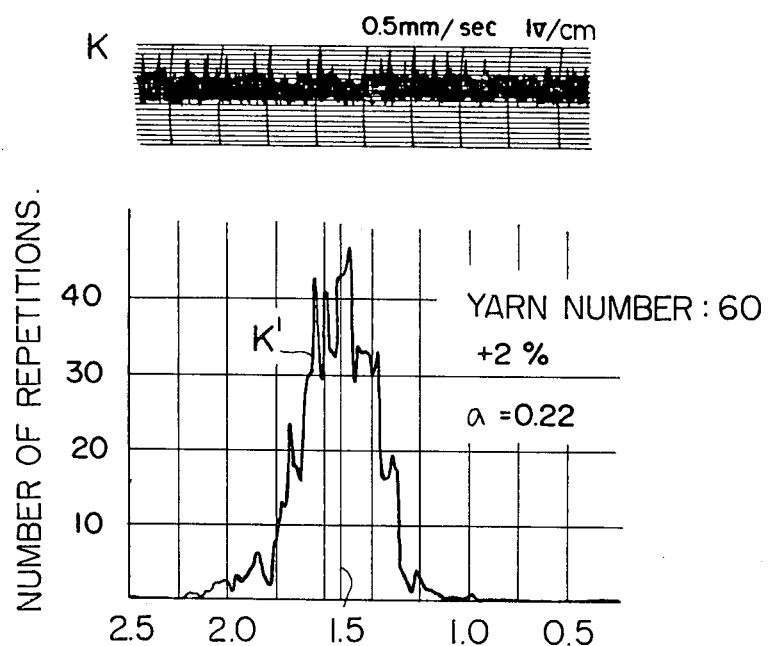
Figure 6D:
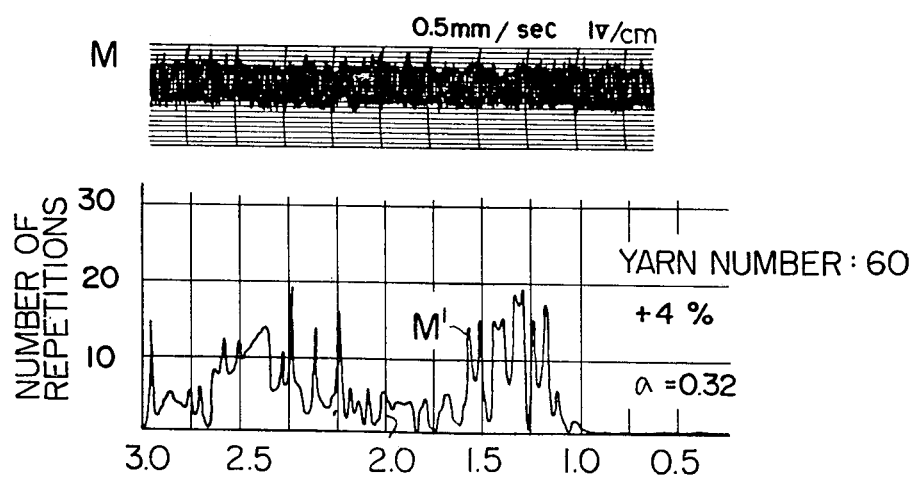

FIG. 5 represents a chart showing the relative relationship of the thus calculated standard deviations. As seen from this Figure, the fluctuation or distribution of the strength-elongation values and that of the corresponding values as found from the distribution charts represents a substantial correspondence. Therefore, it can be definitely concluded that from the frequency distribution which constitutes the core idea of the present invention, possible fluctuation of strength-elongation can be reliably anticipated in advance and in an on-line bases.

In FIG. 6 at J, K, L and M, are several examples of the denier fluctuation of yarns spun and threaded from polyacrylonitrile short length fibers are shown, in the form of electrical output signals from the same capacitive sensor. J' - M' are corresponding amplitude-frequency distribution charts obtained therefrom. It has been determined by comparative experiments that the deviation of the mean value of amplitude frequency distribution is substantially in correspondence to that of the corresponding yarn number counts, being in this case, 1-4%.

Figure 7:
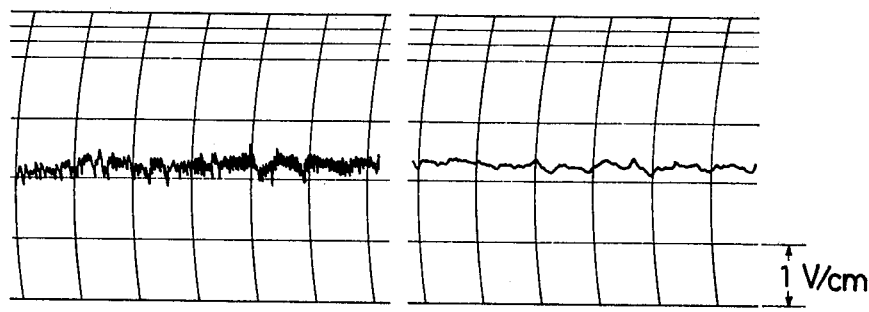
FIG. 7 shows a yarn denier variation curve and a corresponding frequency component distribution chart of a yarn of good quality.

In FIG. 7, at left hand portion, a yarn denier variation curve of a yarn made of polyester (trade name "pewlon"), is shown as output the signal from the capacitive sensor as before. The right hand curve is the same signal after having been passed through a 1 - Hz low pass filter. As seen, this yarn has a relatively good quality.

Figure 8:
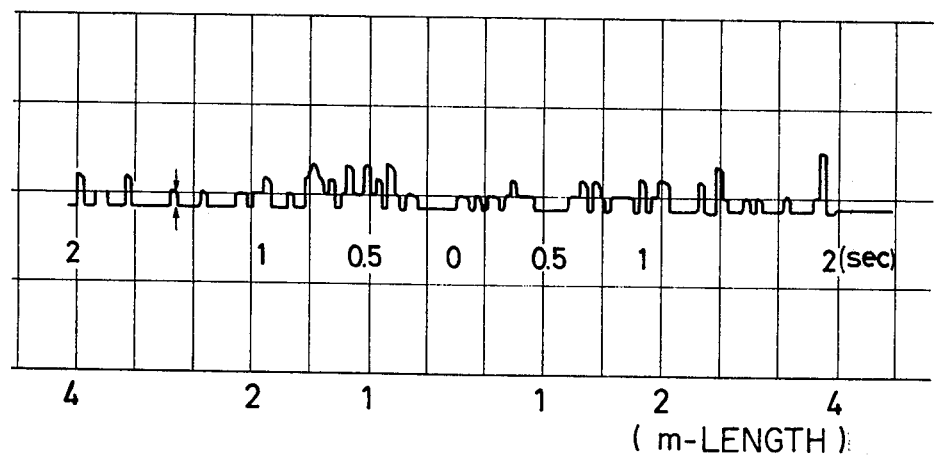
FIG. 8 shows a rather specific similar chart of a yarn of relatively inferior quality.

A corresponding frequency component distribution curve which has been obtained in the similar manner as before is shown in FIG. 8.

Figure 9:
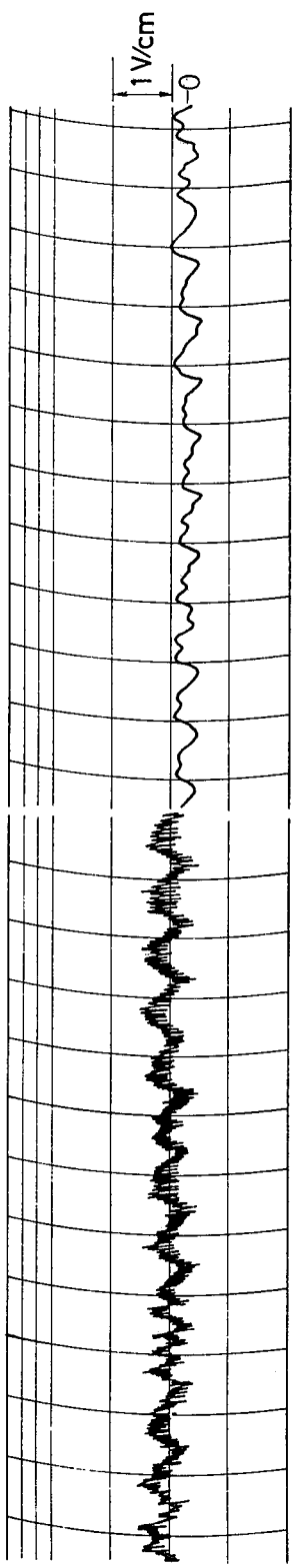
FIG. 9 is a yarn denier variation curve of an unacceptable quality yarn and its corresponding frequency component distribution chart prepared as those of FIG. 7.

Another example similar to that shown in FIG. 7 is demonstrated in FIG. 9. This yarn has a rather inferior yarn quality, as may be well supposed from the drawing. In FIG. 8, the frequency components appear in a rather random manner, from which it can be definitely expected no substantial amount of uneven coloring to appear upon weaving and dyeing of this yarn.

Figure 10:
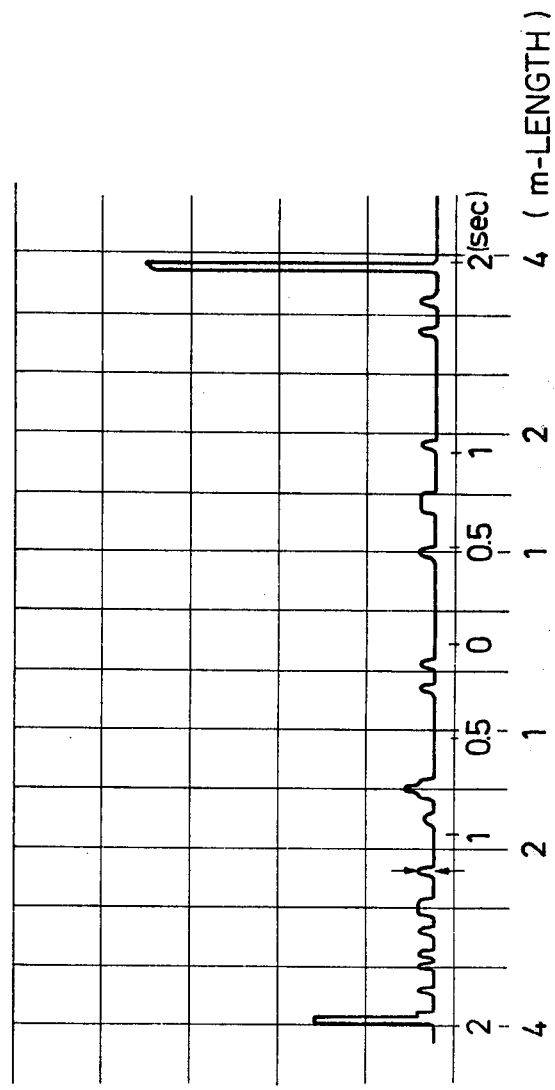
FIG. 10 shows a corresponding frequency distribution chart.

On the other hand, in FIG. 10, frequency components are appearing in a highly localized manner, from which a substantial amount of uneven coloring could occur later and with definiteness.

Figure 20:
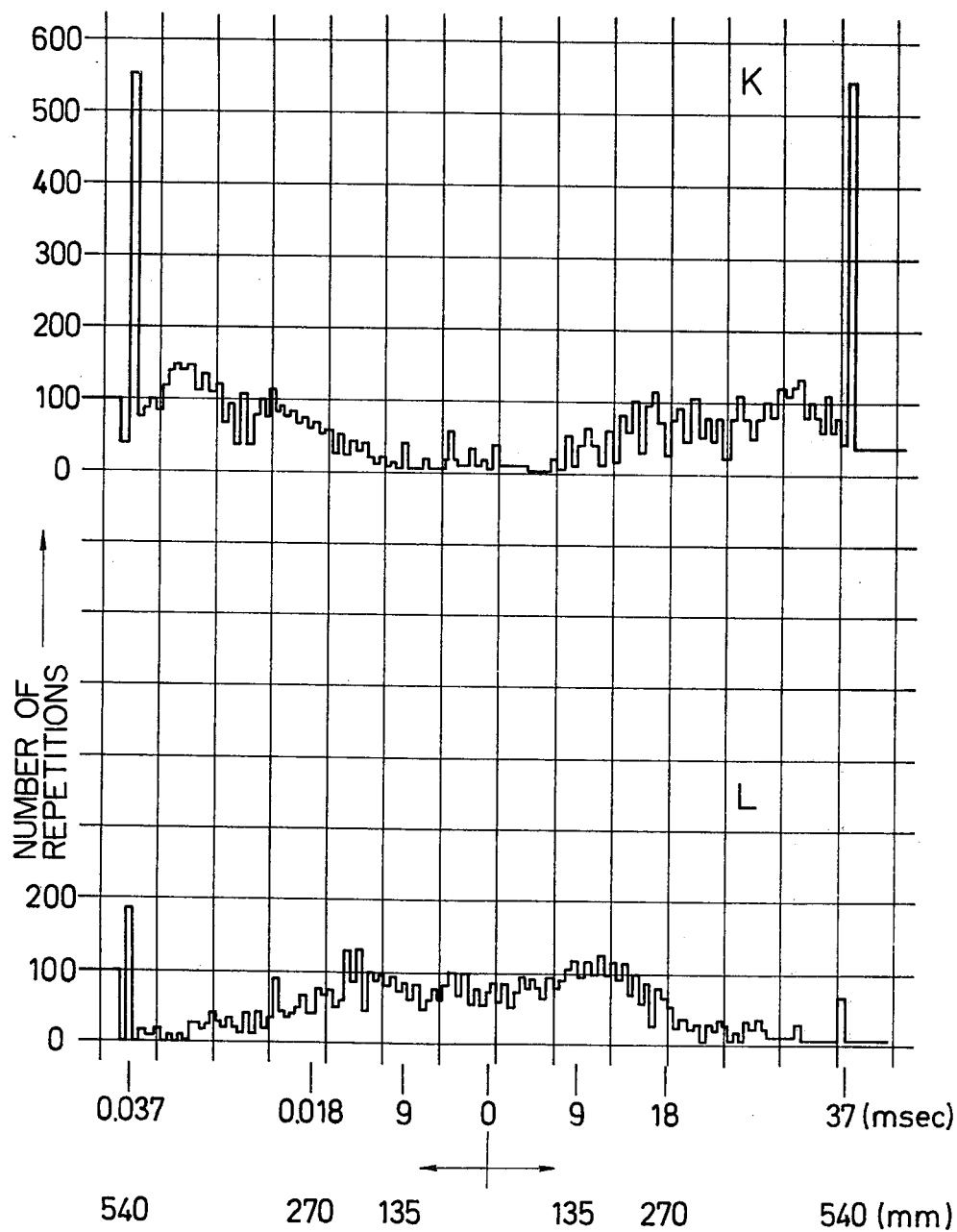

Experimental results of a further polyester yarn, 50d/24f, is shown in FIG. 20, demonstrating its distribution of frequency components. At the lower part L of this drawing, these frequency components are distributed in a rather even manner which means that this yarn is of good quality, demonstrating only a neglegibly small amount of uneven coloring occuring later.

The yarn is conveyed at a speed of 900 meters per minute and the chart corresponds to a yarn length of 225 meters.

In the upper part K of this drawing, a similar distribution curve of frequency components is shown. In this chart, longer period components, less than 27 Hz if expressed in frequency, appear in a highly localized manner. This yarn could show highly inferior uneven coloring after weaving and dyeing later, possibly to a commercially unacceptable degree.

At the yarn part L shown at the bottom of this drawing, the distribution is rather uniform which will result later in the occurrence of small amount of uneven coloring.

In the similar chart shown in FIG. 21, yarn viscous characteristics are overlapped with the occurrence of fluff formation which appears at left zone of the upper curve. The measured polyester yarn length amounted to 225 meters and the number N was 7705. One sampling length amounted to 30 mm. From the results of the upper curve, it may be said that the yarn quality is poor and a fabric made therefrom will show an unacceptably dark dyed color tone, thus being highly defective. On the other hand, the yarn portion represented by the lower curve has such a superior yarn quality which is high enough to be accepted for a commercial purpose.

It is possible to reduce the yarn bulkiness evaluation indices from the foregoing charts J', K', L' and M' shown in FIG. 6.

Figure 16:
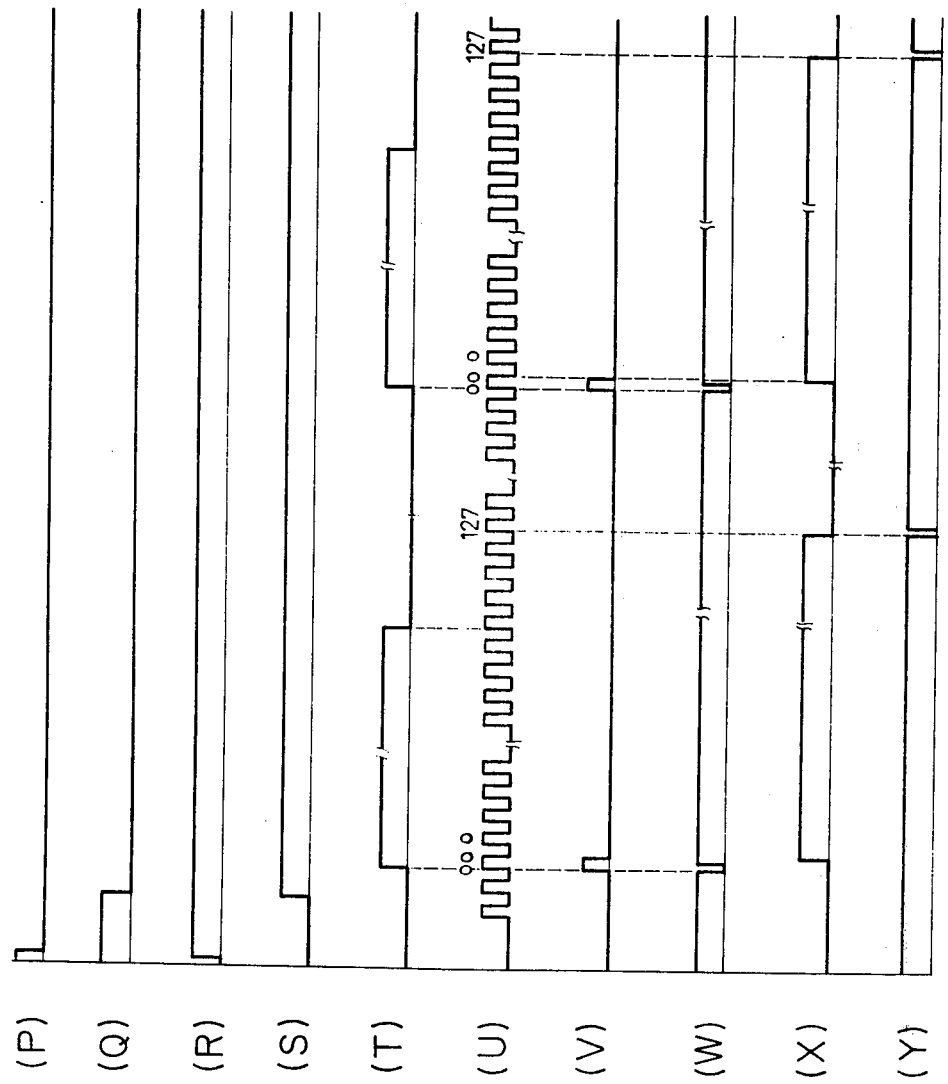
FIG. 16, at (P) - (Q), shows several signal forms appearing at several points of the electronic circuit adopted.

For this purpose, now referring to FIG. 16, there are shown several processed charts from the foregoing. These charts have been prepared by center-to-center overlapping the chart J' upon the respective charts K', L' and M'. The thus produced excess area is shown in each case by being shaded, while the area of chart J' is left in blank. Then, the ratio of the shaded area to the blank area J' is provided which value amounts to 0.33; 0.5 and 0.7, respectively at K", L" and M". According to our experience, this ratio represents the degree of bulkiness of the fiber-spun yarn. According to our experiments with a seriplane tester, a good correspondency has been demonstrated.

The results are shown in the following Table 2.

Table 2

|  | "A" Blank Area | "B" Shaded Area | Ratio of B"/A" | Standard Deviation | Seriplane Evalvation |
|---|---|---|---|---|---|
| J' | 0.6 | 0 | 0 | 0.17 | Class 1 |
| K' | 0.6 | 0.2 | 0.33 | 0.22 | Class 2 |
| L' | 0.6 | 0.3 | 0.5 | 0.27 | Class 3 |
| M' | 0.6 | 0.4 | 0.7 | 0.32 | Unacceptable |

Next, referring to FIG. 12, a preferred embodiment of the apparatus of the present invention will be described in detail.

Figure 12:
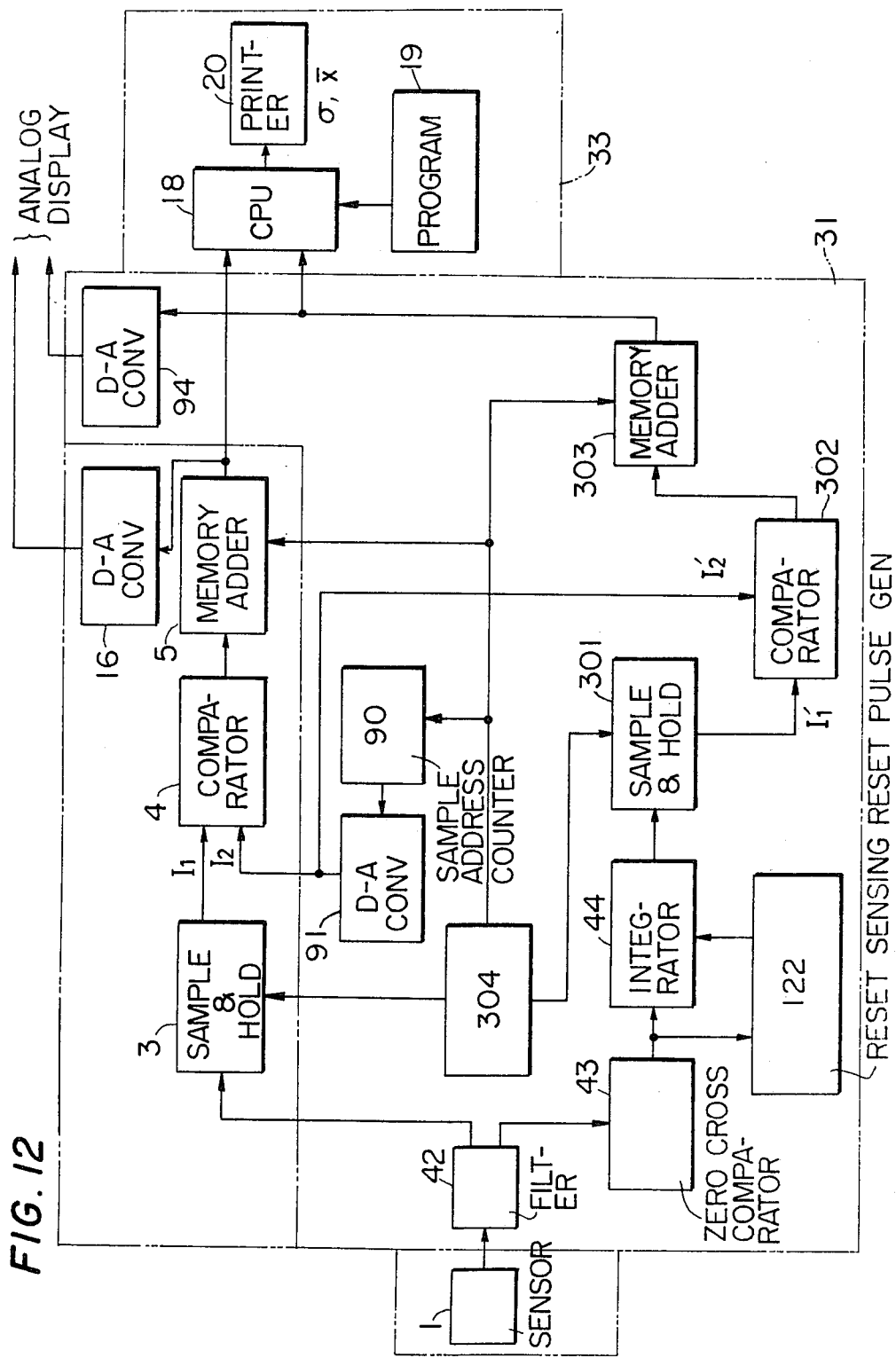
FIG. 12 is a block diagram of the electronic circuit components of the apparatus of the invention.
Figure 13A:
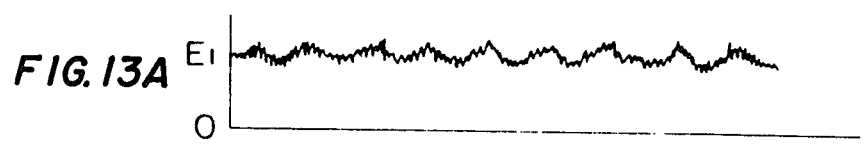
FIG. 13 at (A), (B), (C), (D) and (E), represents several signal forms appearing in the electronic circuit.
Figure 13B:
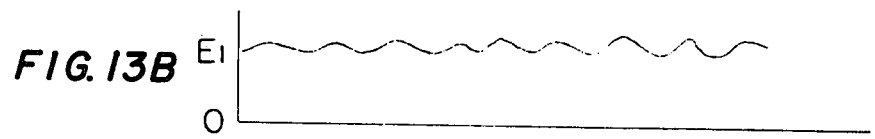
Figure 13C:
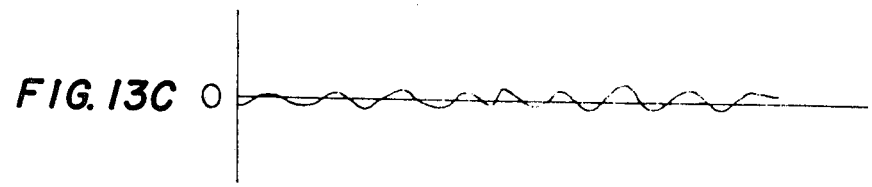
Figure 13D:
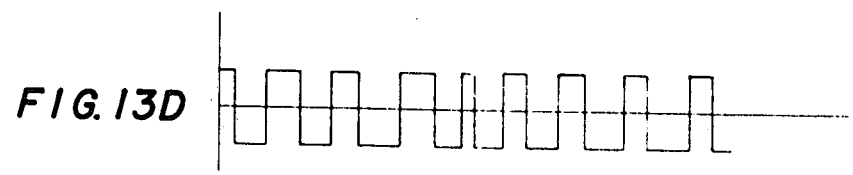
Figure 13E:
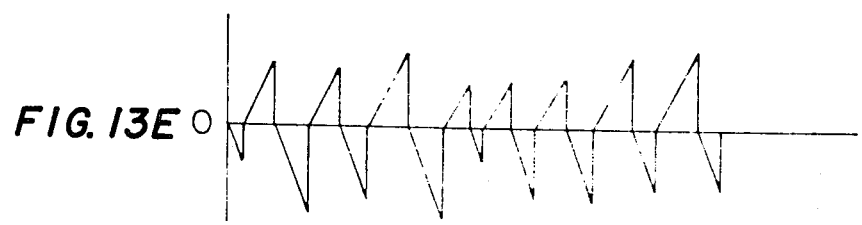
Figure 17:
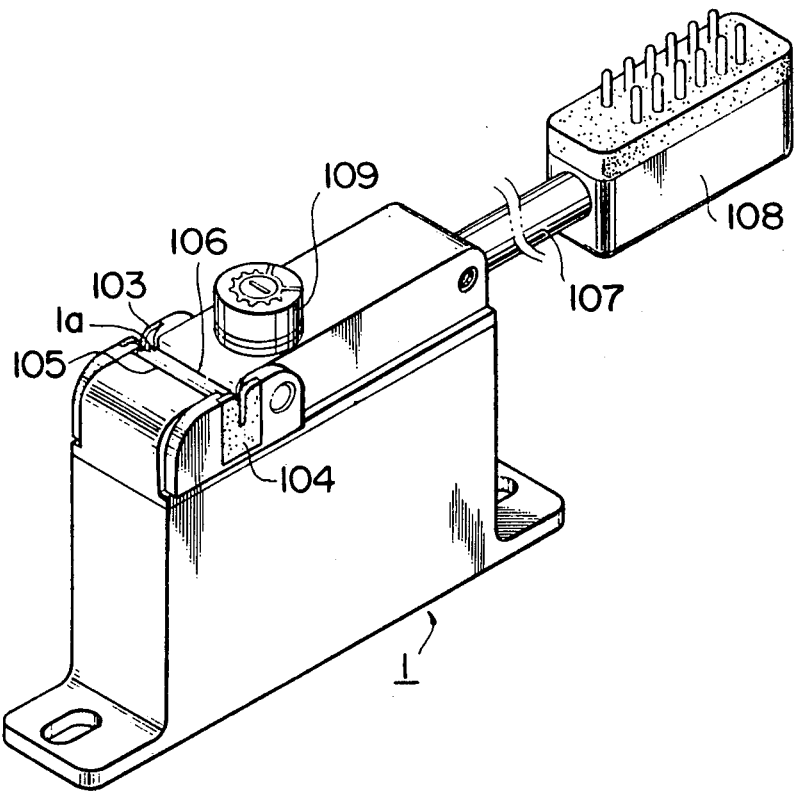
FIG. 17 is a perspective view of a capacitive sensor unit adopted as part of the inventive apparatus.

In FIGS. 12 and 17, numeral 1 represents a capacitive sensor unit employed in the invention.

Figure 11:
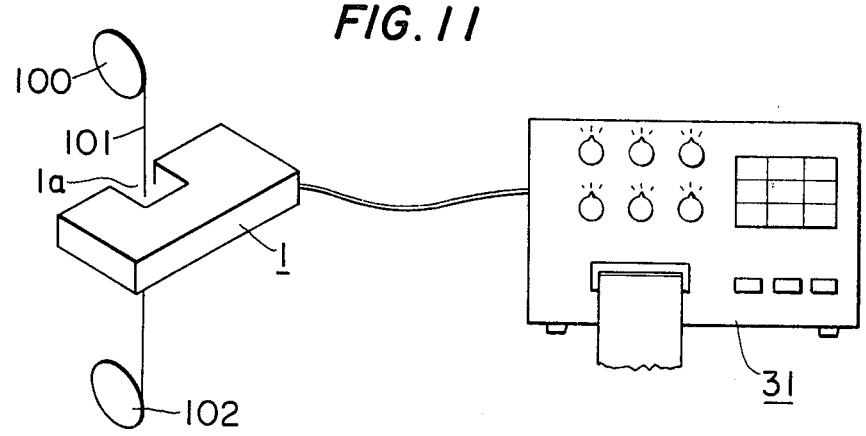
FIG. 11 is a schematic outside view of an embodiment of an embodiment of the apparatus according to this invention.

Symbol 1a represents a yarn passage opening defined by the gap of a pair of capacitor electrodes. Numeral 101 represents a yarn under test which is taken out continuously from a delivery reel 100 and passed through the condenser gap 1a. The tested yarn is continuously wound on a winding reel 102. Numeral 31 in FIG. 11, represents a signal processor which contains the components shown in FIG. 12.

Numeral 33 in FIG. 12, represents a calculating section which operates in the manner to be later described.

The electrical output signal delivered from the sensor 1 is fed to a filter 42 which may be a low pass, high pass or band pass filter, so as to adapt it to the desired kind of job to be executed, thereby removing unnecessary signals therefrom.

As an example, at the present stage, the job may be assumed to be amplitude component distribution. For this purpose, output signal from filter 42 is fed to a sampling and hold circuit 3 wherein the signal is converted into a sampling signal which is then brought to a comparator input $I_1$ of a comparator 4. The latter has a second input $I_2$. A sampling synchro-signal generator 304 delivers a series of clock pulses which is fed to a memory adder 5 which is thus driven stepwise. A ramp voltage in relation to the number of addresses contained in the adder 5 is applied to the second input $I_2$. For this purpose, a sampling counter 90 is provided and connected as shown, so as to count drive clock pulses applied to the adder 5, thus acting as a kind of memory address counter. The thus counted value is fed to a D-A converter 91 which serves for converting the digital value into a corresponding analog signal which is then supplied to $I_2$ of the comparator 4 as its comparative standard ramp input voltage. At the comparator 4, the first input through $I_1$ is compared through $I_2$ with the ramp voltage, so as to find out a coincidence point within the voltage width of the ramp. Upon attaining such a coincidence point, a coincidence signal is delivered from the output of the comparator 4. By application of the coincidence signal, a binary 1 will be added at the memory address in the memory adder 5.

At each arrival of a sampling signal of the above kind, the aforementioned operation will be repeated and in this way, an amplitude frequency distribution derived from the electric output signal from the sensor unit is accumulated in the memory 5. This distribution could naturally be taken out from the memory 5 by successive read-out operations.

Next, the adopted structure for deriving the frequency component frequency distribution from the sensor output signal will be described. In this case, the sensor output signal is passed through a filter 42 which may be a high pass or band pass type, adapted for removal of the d.c. components and unwanted components. The thus filtered signal is fed to a zerocross comparator 43 as its input. This comparator is so designed and arranged to make a comparison at zero point of the signal and based upon the polarity-reversed component of the signal, to convert the latter into a rectangular wave signal having a duration period corresponding to zero-to-zero time length of the signal. Of course, in place of the zero-to-zero interval, the peak-to-peak duration can be adopted.

The rectangular wave signal convertedly produced at zero-cross comparator 43 is fed to an integrator 44 for being integrated therein. The integration constant of this integrator is made variable, so as not to be saturated even with the application of a possible long frequency signal component. Leading and trailing points of each rectangular wave signal are fed from the comparator 43 for resetting the integrator 44. A 1 from the integrator 44 is converted into a sampling signal at the circuit 301 depending upon the constant frequency period generated at and delivered from the sampling frequency signal generator 304.

The sampling signal converted at and delivered from sample and-hold circuit 301 is fed to the first input of comparator 302. The output from D-A converter 91 is fed to the second input of comparator 302. Comparator 302 will perform a similar operation as the comparator 4. With feeding of a coincidence signal, the memory address of memory adder 303 is added with a binary 1.

The above mentioned operation will be repeated for each arrival of the sampling signal and thus, the similar accumulation job is performed at the memory of the adder 303; and so on.

The amplitude component frequency distribution accumulated at memory adder 4 and the frequency components frequency distribution accumulated at memory adder 303 are converted into their corresponding analog sampling signals at respective D-A converters 16 and 94 for later utilization for the purpose of respective wave pattern observation. For satisfying these functions, memory adders 5 and 303 may be united into an overlapped stack assembly of MOS-type shift registers.

It can be easily carried out to perform respective write-in and read-out functions to and from this memory by driving shift registers with clock signals made in synchronism with output signals from sampling synchro-signal generator at 304.

Digital data at memory adders 5 and 303 may be transferred as per se to an electronic computor CPU 18 which is fitted therein with an operation control unit adapted for performing operations under the instructions from a programmed signal generator 19, so as to perform a printing function by means of a digital type printer 20.

With the arrangement referred to hereinbefore, the amplitude component frequency distribution as the contents of memory adder 5 and the frequency component frequency distribution as the contents of memory adder 303 may be processed to find the current mean value $\bar{x}$ and the current standard deviation Y.

Since these calculated values are based upon the measured values taken from the sample material for a certain time period, specific and reliable evaluation standard can naturally be provided.

FIG. 13, shows several wave forms of preferred output signals delivered from selected circuit components of the circuit arrangement shown in FIG. 12.

More specifically, (A) represents the output signal from the sensor unit 1. (B) and (C) represent representatively and by way of example, two output signal waves from filter 2. (D) represents the output from zero-cross comparator 10. (E) represents the output from the sample-and-hold circuit 13.

Figure 14:
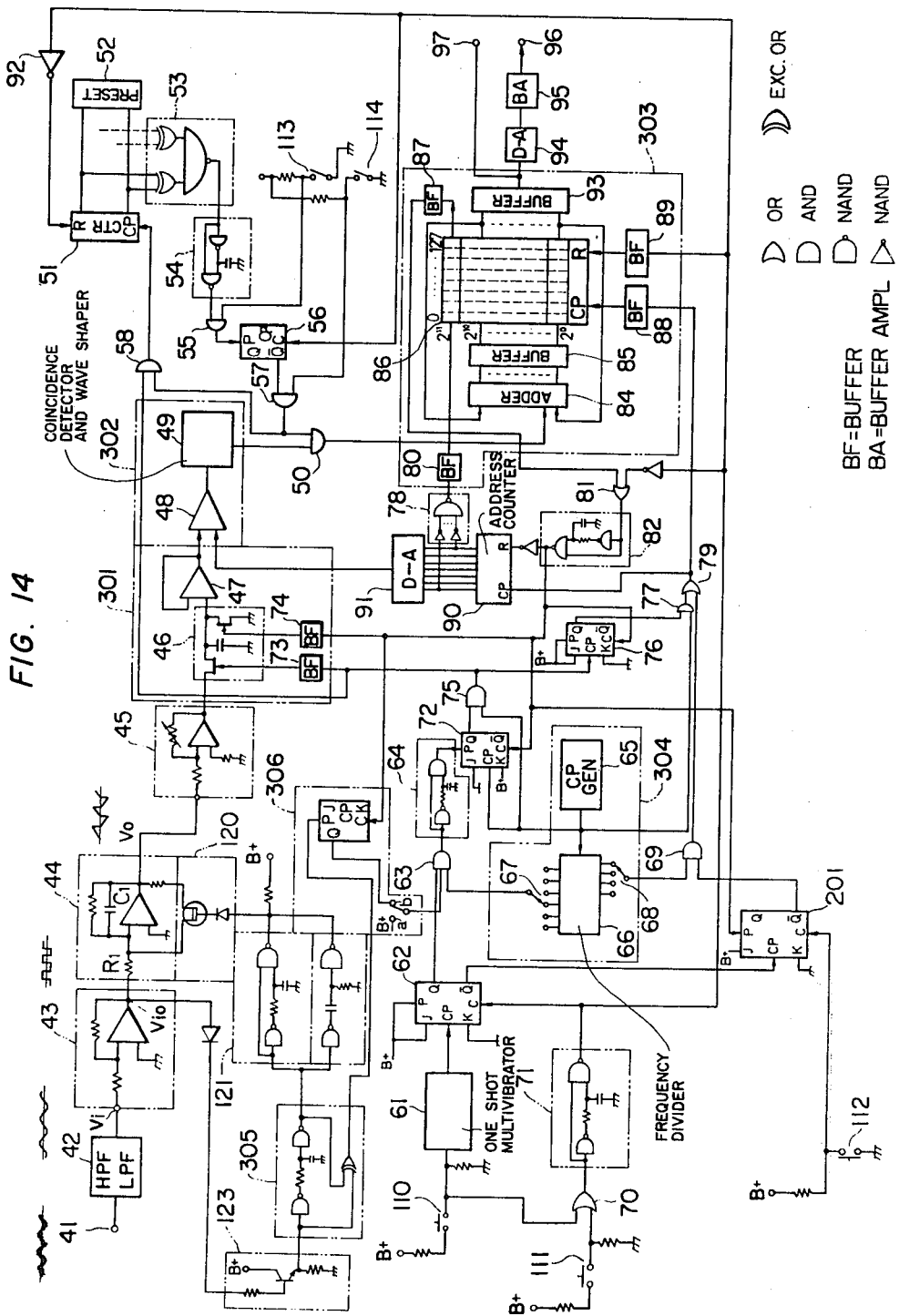
FIG. 14 is a more specific representation of the electronic circuit included in the apparatus of the present invention.

Next, referring to FIG. 14, an embodiment is shown of means adapted for extracting the frequency component frequency distribution.

An electric signal fed to a terminal 41, which is electrically connected to a sensor unit such as that shown at 1 in the foregoing, is passed through a high pass and low pass filter 42 for removal of unnecessary frequency components therefrom. This filtered signal is converted into a rectangular signal at a zero-cross comparator 43. The output from the comparator 43 is subjected to a level conversion at voltage level converter 123 and then conveyed to short pulse generators 121 and 122, so as to deliver a short pulse at each of the leading and trailing edges of the rectangular signal. By the use of this short pulse, the electrical charge at the condenser C1 of the integrator 44 is caused to discharge towards P-channel field effect transistor switch 120. The short pulse width is designed to have a duration less than 1/10 or still shorter than the input electrical signal and current content at the said field effect transistor switch 120.

With the above structure and arrangement of the various circuit components employed, the rectangular signal as an output from the zero-cross comparator 43 and in relation to the frequency component contained in the electrical signal at terminal 41 is converted at the integrator 44 into an integrated wave form in relation to the frequency component while being subjected to resetting at each of the leading and trailing edges of the rectangular signal. The thus integrated wave form is fed through amplifier 45 to sample-and-hold circuit 46 and converted thereat into a sampling signal in dependence to a sampling time specified by a frequency divider 66. The sample-and-hold signal at the circuit 46 will be fed to one input of comparator 48 through buffer amplifier 47. To another input of comparator 48, is supplied the output from address counter 90 which serves for counting the addresses of MOS-type shift register 86, and after converted into a corresponding analog value at D-A converter 91. Therefore, the shift register 86 is arranged to act as a memory, and a voltage in relation to the address is applied to the comparator 48 and as the comparing ramp voltage. By adopting this means, a comparison is made with the signal incoming through buffer amplifier 47 and when a coincidence point is brought about, a coincidence signal pulse will be generated at the coincidence-detecting and wave shaping circuit 49. This coincidence signal is supplied to AND-gate 50 and when the latter is at its opened state, it will apply an input the lower bit in the adder 84. By this operation, a binary 1 will be added at the address section of MOS-type shift register 86.

The embodiment of shift register 86 shown in FIG. 14 has 128 address bits multiplied by 12 memory bits. The memory section is so designed and arranged that signals are caused to circulate in parallel through the adder 84.

When start switch 110 is turned on, the entire circuit is brought into its reset position. A delay is brought about by the one shot multivibrator 61, so as to bring flip-flop 62 into its operative position. With the output Q of flip-flop 62 at the binary 1-level, the signal generated at and delivered from clock generator 65 is subjected to frequency division by frequency division circuit 66 and selected at sampling selection switch 67 and further supplied to AND-gate 63 which is preset by the signal delivered from start pulse generator 305 which is designed and arranged to do so at its peak point which corresponds substantially to that of peak voltage signal from the integrator 44. With each start pulse delivered, flip-flop 306 will generate one mode gate signal. When a binary 1 has been supplied from flip-flop 62 and so far as the latter is caused to reset, the sampling time pulse selected by sampling time selection switch 67 is allowed to pass.

The signal is then converted through single pulse converter 64 into a short pulse and conveyed to P-terminal (for preset use) of the next stage flip-flop 72, and thereby the Q-terminal of flip-flop 72 is brought to the 1-level. On the other hand, the clock pulse from clock generator 65 is supplied to the CP-input of flip-flop 72, and thereby the Q-terminal of flip-flop 72 is brought again to the 0-level. A single pulse in relation to this clock pulse is used for sampling purposes of the sample-and-hold circuit 46. This pulse is applied to sample number counter 51.

Further, this pulse is used as an input clock pulse to flip-flop 76 and at the trailing edge of this pulse, the Q-terminal of flip-flop 76 is brought to the 1-level. With realization of this state, AND-gate 77 is opened and thus, the clock pulse from clock generator 65 will begin to drive concurrently both MOS-type shift register 86 and address counter 90.

With the count of the address counter being zero, a signal will be delivered from zero-value detector circuit 78 and conveyed to 2"-bit-section of MOS-type shift register 86. Thus, the clock pulse is conveyed through buffer 88 for driving the MOS-register, the shift operation being carried out to the address 128. Upon entrance of 128 clock pulses, a single pulse is generated at the generator 82 and conveyed through buffer 87 and OR-gate 81. Then, address counter 90, hold section of sample-and-hold circuit 46 and flip-flops 72, 76 and 306 are reset.

By these operations, the related arrangement is brought again to the sampling state, and the above operation is repeated. Since the number of samplings has been counted at the counter 51 provided for this purpose, it is possible to stop any further increase in the sampling number in an automatic way when it attains the present value of 52. In this case, automatic stop switch 113 is turned off. Or alternatively, a provisional stop switch is turned on for provisionally stopping the sampling operation.

The further value stored in MOS-type shift register 86 after the above stoppage of sampling, may be taken out as an output in a digital form via buffer 93, or in an analog form via D-A converter 94, so as to be utilized for various operational or observational purposes as desired.

The shift operation at this time of MOS-shift register 86 is brought about by such operation that the clock pulse from the generator 65 is subjected to a frequency division at the divider 66 and the thus provided synchlorizing signal is selected at the switch 68 and conveyed through AND-gate 69 to the shift register 86.

The starting operation at this time may be initiated by the operation of flip-flop 201 controlled by a low speed start switch 112 such as a push button.

Several representative wave forms as appearing in the circuit arrangement shown in FIG. 14 are demonstrated.

The first signal Vi represents by way of example the output signal of the filter 42.

The second signal Vio is the output from the zero-cross comparator 43. The third one is the reset which are delivered from reset pulse generator 121 or 122 and used for the foregoing signal $V_O$.

The fourth signal $V_O$ represents the output from the integrator 44.

FIG. 16 represents a timing chart for the circuit arrangement shown in FIG. 14.

The first signal at (P) represents a start signal of start switch 110. The second signal at (Q) is an output signal from one shot multivibrator 61.

The third signal at (R) is an output from single pulse generator 71. The fourth signal at (S) is an output from flip-flop 62.

The fifth signal at (T) is an output from frequency divider 66 at its sampling selection switch side. The sixth signal at (U) is an output series of clock pulses from the generator 65.

The seventh signal at (V) represents an output from flip-flop 72 at Q. The eighth signal at (W) is an output from single pulse generator 64.

The ninth signal at (X) is an output from flip-flop 76 at Q. The tenth signal at (Y) represents an output from single pulse generator 82.

In FIG. 17, the sensor unit 1 is shown in its enlarged perspective view. This sensor 1 is connected with a terminal box 108 carrying a number of input and output terminals.

Figure 19:
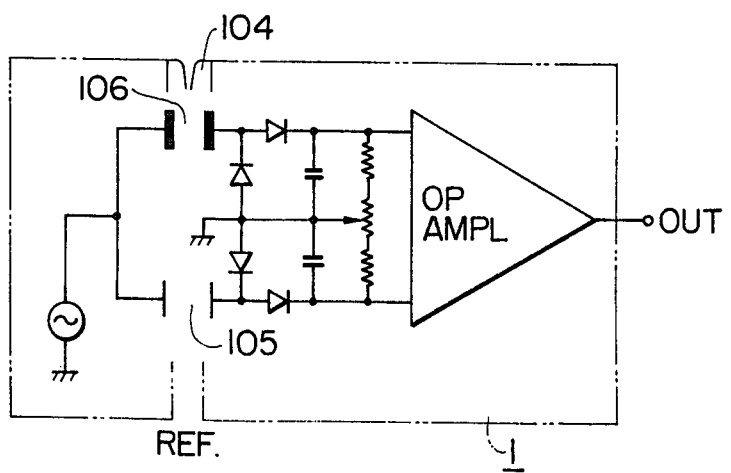
FIG. 19 is a simplified circuit arrangement of the apparatus of the invention.
Figure 18A:
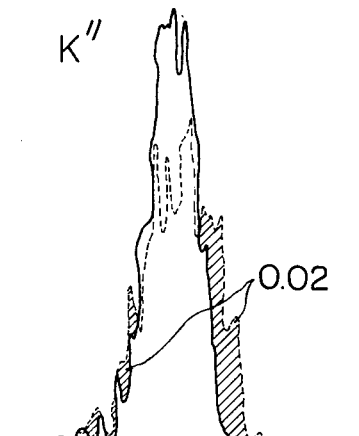
FIG. 18, at K", L" and M", shows several charts, showing how to determine the degree of bulkiness of a yarn according to the inventive technique.
Figure 18B:
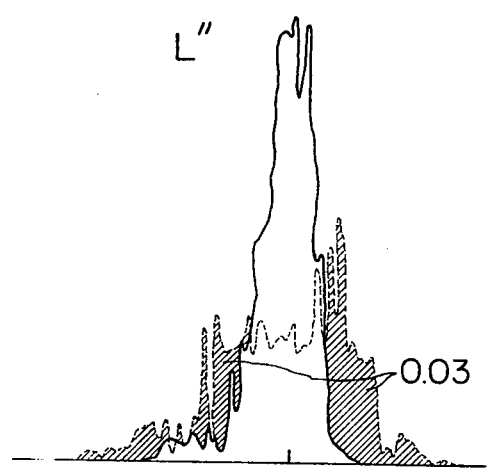
Figure 18C:
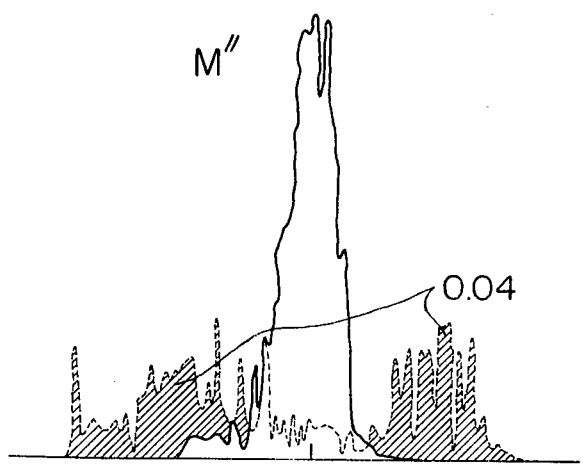

Symbol 1a represents the condenser gap adapted for passage of the yarn 101, specifically shown in FIG. 11. Condenser electrodes 105 and 106 define the yarn passage gap. 103 and 104 represent two stationary yarn guides positioned at both ends of the gap. Numeral 107 represents a conducting cable arranged for electrical connection between the sensor and terminal box. Numeral 109 is a screw adjuster by which the condenser gap may be adjudged in its width as desired. The sensor and its related several main components are schematically shown in FIG. 19 which may be self-explanatory.

From the foregoing disclosure, any reader can well understand the nature and effects of the apparatus of the present invention.

The embodiments of the invention in which an exclusive property or privilege is claimed are as follows:

1. An apparatus for evaluating the characteristics of a continuous yarn, said apparatus comprising:
   a. sensor means for sensing a property of the yarn and for producing a first signal in response thereto;
   b. first circuit means coupled to said sensor means for receiving said first signal and for producing a second signal which is a function of the amplitude component frequency distribution of said first signal;
   c. second circuit means coupled to said sensor means for receiving said first signal and for producing a third signal which is a function of the frequency component frequency distribution of said first signal; and
   d. calculating means coupled to said first and second circuit means for receiving said second and third signals and for calculating the mean value and standard deviation of each of said signals.

2. The apparatus of claim 1 wherein said first circuit means comprises:
   a. a sample and hold means coupled to the output of said sensor means;
   b. ramp signal generator means;
   c. comparator means coupled to the output of said sample and hold means and said ramp signal generator means for receiving the outputs thereof and for generating an output upon the coincidence thereof;
   d. memory adder means coupled to the output of said comparator means, wherein the output of said memory adder means is applied to said calculating means.

3. The apparatus of claim 1 wherein said second circuit means comprises:
   a. a zero crossing detector means coupled to said sensor means for producing a rectangular output signal in accordance with the zero crossings of the output of said sensor means;
   b. integrator means coupled to said zero crossing detector means for integrating the output thereof;
   c. sample and hold means coupled to the output of said integrator means for receiving the output thereof;
   d. ramp signal generator means;
   e. comparator means coupled to the output of said sample and hold means and said ramp signal generator means for receiving the outputs thereof and for generating an output upon the coincidence thereof; and
   f. memory adder means coupled to the output of said comparator means, wherein the output of said memory adder means is coupled to said calculating means.

4. The apparatus of claim 1 wherein said sensor means comprises a capacitive sensor and a filter means coupled thereto.

* * * * *